United States Patent [19]

Kapitanov et al.

[11] 4,244,372

[45] Jan. 13, 1981

[54] SURGICAL INSTRUMENT FOR SUTURING ORGANS

[76] Inventors: Nikolai N. Kapitanov, ulitsa Levchenko, 3, kv. 9; Vladimir M. Fedotov, ulitsa Startovaya, 21, kv. 42; Natalya P. Petrova, 1 Novokuzminskaya ulitsa, 4, kv. 40; Marya D. Patsiora, ulitsa Sokolnichesky val, 40, kv. 106; Kim N. Tsatsanidi, ulitsa Sokolnichesky val, 40, kv. 77; Oleg B. Milonov, Leninsky prospekt, 93, korpus 4, kv. 4, all of Moscow, U.S.S.R.

[21] Appl. No.: 15,654

[22] Filed: Feb. 27, 1979

[30] Foreign Application Priority Data

Mar. 31, 1978 [SU] U.S.S.R. .................. 2595728

[51] Int. Cl.³ .................................. A61B 17/04
[52] U.S. Cl. .................. 128/334 R; 227/DIG. 1; 227/152
[58] Field of Search ............ 227/19, 152, DIG. 1; 128/334 R

[56] References Cited

U.S. PATENT DOCUMENTS

| 3,079,606 | 3/1963 | Bobrov et al. | 227/19 |
| 3,317,105 | 5/1967 | Astafjev et al. | 227/DIG. 1 |
| 3,490,675 | 1/1970 | Green et al. | 227/19 |

FOREIGN PATENT DOCUMENTS 2619681 of 1976 Fed. Rep. of Germany ............ 227/19

OTHER PUBLICATIONS

"Surgical Stapling", Scientific American, Mallina et al., Oct. 1962, vol. 207, No. 4, pp. 48–56.

Primary Examiner—Robert W. Michell
Assistant Examiner—C. W. Shedd
Attorney, Agent, or Firm—Holman & Stern

[57] ABSTRACT

The instrument comprises a supporting part and a staple-receiving part connected pivotally to each other, their working ends carrying opposing longitudinal jaws. The longitudinal jaw of said staple-receiving part accommodates staple magazines. Made in said staple magazines in opposition to the staple-clinching indentations of the longitudinal jaw of the supporting part are transverse slots adapted to accommodate the members for driving said staples and said staples, and longitudinal slots adapted to accommodate bars with wedge-shaped ends facing said staple-driving members, adapted for cooperation with said staple-driving members, to drive out and insert said staples. The longitudinal slot of said staple-receiving part movably accommodates a knife blade movable jointly with said bars. The instrument includes a latch-type lock for retaining the two parts in a position where they are brought together to define a suturing gap therebetween, and means for preventing substantial traumatism of the layer-by-layer sutured organs and for ensuring the rigidity of the suturing unit of the instrument in the course of a suturing operation.

1 Claim, 6 Drawing Figures

SURGICAL INSTRUMENT FOR SUTURING ORGANS

BACKGROUND OF THE INVENTION

This invention relates to medical instrumentation, and more particularly to a surgical instrument for suturing organs.

The invention can be used for resection of portions of organs with suturing of the remaining and removed parts of an organ, e.g. of a lung and other organs. However, the disclosed instrument can also be utilized to utmost effectiveness for conducting liver resections.

At present, liver resection surgery is performed purely manually, which takes a relatively long time (thus, in a single take there is resected a liver portion 5 to 8 mm long and 8 to 10 mm thick, with ligation of the vessels and ducts to both sides of the resection area), to say nothing of the operation more often than not being associated with considerable loss of blood and post-operational complications of various kinds.

There is known a surgical instrument for simultaneous resection of soft tissues and their suturing (cf. the U.S. Pat. No. 3,079,606, dated Mar. 5, 1963), usually employed for placing gastro-intestinal anastomoses. The instrument includes two pivotally connected parts, viz. a support part and a staple-receiving part, the two parts carrying at the working ends thereof opposed longitudinally extending jaws. The longitudinally extending jaw of the supporting part has made therein a longitudinal array of indentations for clinching the staples, i.e. for bending over the ends of the legs of the staples. The longitudinally extending jaw of the staple-receiving part carries staple magazines wherein, in opposition to the abovementioned indentations, there are made transverse slots for staples, accommodating therein staple drivers and staples. Each staple magazine has made therein longitudinal slots accommodating bars with wedge-shaped ends facing the staple drivers and adapted for cooperation with the staple drivers when the staples are driven out. The staple-receiving part has also made therein a longitudinal slot accommodating a knife blade for tissue-dissecting purposes, which is longitudinally movable jointly with the said bars. The staple-receiving and support parts in their operating position where they are brought together to define a suturing gap therebetween are retainable with a self-actuating locking device.

The hitherto known instrument is mainly intended for placing interintestinal juice anastomoses and operates, as follows. The longitudinal jaws of the instrument are inserted into the interior of the intestines which are to be sutured, through incisions made in the walls of the intestines, and the walls to be sutured are positioned between the longitudinal jaws which are in the spread position.

The two parts of the instrument are connected with the pivot, and the support and staple-receiving parts are relatively rotated to bring together their longitudinal jaws disposed on the working ends of these parts, until the suturing gap is defined therebetween, whereafter the two parts are locked with the locking device.

The bars with the knife blade are moved toward the longitudinal jaws, with the bars engaging by their wedge-shaped ends the staple-driving elements or drivers, whereby the drivers are moved along the slots in the staple-receiving part. Upon leaving the transverse slots, the staples pierce the tissue with their legs or prongs and engage the indentations or anvils in the jaw of the supporting part, whereby the staples are bent into a generally B-shape, firmly securing the tissue.

Simultaneously, the moving knife blade severs the tissue between the sutures. Following the suturing procedure, the supporting and staple-receiving parts are unlocked, and the instrument is removed from the suturing position. In this manner the intestinal walls have become sutured, and a clearance has been provided between the sutures to ensure the permeability of the intestine. The incisions in the intestinal walls, left after the withdrawal of the longitudinal jaws, are sutured by conventional suturing operation.

The structure of the suturing unit of the instrument provided for rapid placing of sutures on the remaining and removing portions of the organ, with simultaneous severing of the tissue between the rows of the staples, i.e. between the sutures. The instrument is operable for suturing and resection of liver portions as great as 15 to 20 mm.

However, the instrument would not provide for performing resection of a liver thicker than 20 mm, whereas the thickness of the human's liver varies, with the sectional dimension of its different portions being as great as 60 to 70 mm and even greater. Should a greater thickness than 20 mm be engaged by the instrument, it would result in the breakage of the capsule and of some of the vessels and ducts, bringing about intense blood loss.

Layer-wise or level-wise suturing, i.e. suturing of a greater thickness of the liver in several layers, with piercing the capsule by the longitudinal jaw of the supporting part and successively engaging each 15 to 20 mm thick layer, is impossible on account of the considerable cross-sectional size of the longitudinal jaw, the piercing and insertion of the longitudinal jaw resulting in substantial trauma and intense blood loss. On the other hand, a reduction of the cross-sectional dimensions of the longitudinal jaw of the supporting part of the hitherto known instrument cannot be attained, since this part takes up the load at stapling, and its reduction could bring about its considerable bending deformation yielding drastic impairment of the suture quality.

Furthermore, with the knife blade of the known instrument moving, there is sometimes observed the phenomenon of the resected tissue being dragged along by the blade throughout the entire length of the longitudinal jaws, which results in impaired quality of the severing and in trauma of the tissue adjoining the suture.

It can therefore be seen that the hitherto known instrument cannot effectively be used for performing resections of the liver in the layer-wise fashion when the liver is of a considerable thickness, i.e. in the majority of the portions of the liver.

It is an object of the present invention to provide a surgical instrument for suturing organs, which can perform layer-by-layer suturing and resection of a parenchymal organ of a considerable thickness, with minimized traumatism of this organ.

SUMMARY OF THE INVENTION

The invention provides a surgical apparatus for suturing organs, e.g., parenchymal ones, comprising two pivotally connected parts, viz. a staple-receiving part and a supporting or clinching part, the parts having respective working ends carrying opposing longitudinal jaws, the longitudinal jaw of the supporting part having indentations made therein for bending over the ends of the legs of staples, and the longitudinal jaw of the staple, receiving part carrying staple magazines wherein transverse staple-receiving slots are made in opposition to the said indentations, the slots accommodating therein the staples and staple drivers, and longitudinal slots adapted to accommodate therein bars with wedge-shaped ends facing the staple drivers and being adapted for cooperation with the staple drivers to drive out the staples, a knife blade being accommodated in a longitudinal slot in the staple-receiving part for motion jointly with said bars, and a locking device for retaining the two parts in a position where they are brought together to define a suturing gap, in which instrument, in accordance with the invention, means are provided for preventing substantial traumatism of layer-by-layer sutured organs and ensuring the rigidity of the suturing part of the apparatus in the course of the suturing operation.

The herein disclosed surgical instrument is able to solve the problem of layer-by-layer resection of parenchymal organs of a considerable thickness, sufficiently rapidly, with high quality and substantially without blood loss; the instrument being fit for a wide field of applications for performing surgery on the liver, spleen, lungs, and other kinds of surgery.

It is expedient that the means for preventing substantial traumatism of the layer-by-layer sutured organs and ensuring the rigidity of the suturing part of the apparatus in the course of the suturing operation should include rods mounted on the longitudinal jaw of the staple-receiving part and adapted for cooperation with the longitudinal jaw of the supporting part, shaped as a bar, with the aid of openings made in said bar-shaped jaw and of a locking strip accommodated in the longitudinal slot of the bar-shaped jaw and having apertures alignable with said openings and corresponding to the spacing of the rods, the rods having grooves made therein, adapted to be engaged by the apertures of the locking strip.

With the suturing unit of the instrument having the abovedescribed structure wherein the longitudinal jaw of the staple-receiving part has mounted therein the rods cooperating through the locking strip with the longitudinal jaw of the supporting part, it becomes possible to minimize the cross-sectional dimensions of the last-mentioned jaw, whereby the longitudinal jaw of the supporting part can be introduced into a parenchymal organ substantially without injuring the latter and causing blood loss, with the overall rigidity of the suturing unit of the instrument adequately maintained. Furthermore, the quality of the resection is enhanced owing to the cooperation between the knife blade and the rods, the vessels and ducts being sutured becoming grouped within the confined spaces intermediate the rods, so that no dragging of the resected tissue by the blade occurs.

The design of the instrument is simple and reliable, and its operation can be easily mastered by a surgeon.

BRIEF DESCRIPTION OF DRAWINGS

The present invention will be further described with reference being had to the accompanying drawings, wherein.

DESCRIPTION OF PREFERRED EMBODIMENT

Figures 1, 2:
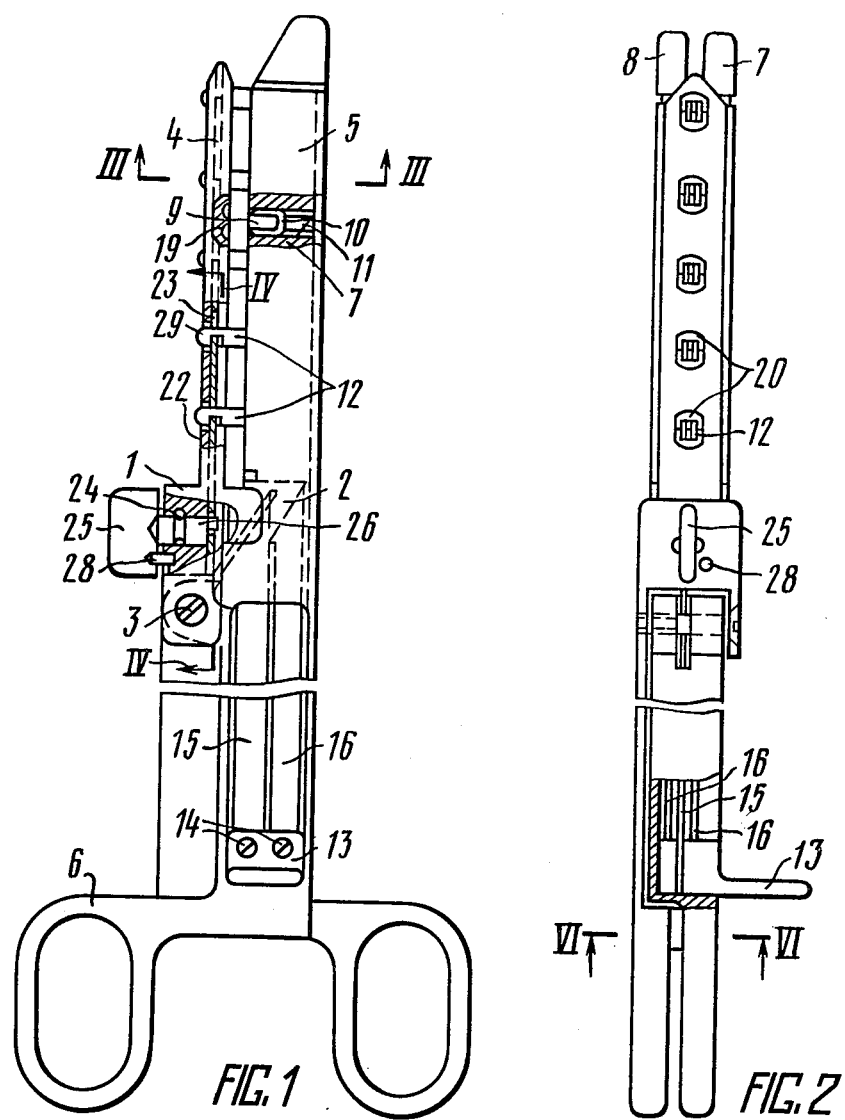
FIG. 1 is a top plan view of a surgical instrument for suturing organs, embodying the invention.
FIG. 2 is a side elevation of the instrument.
Figure 3:
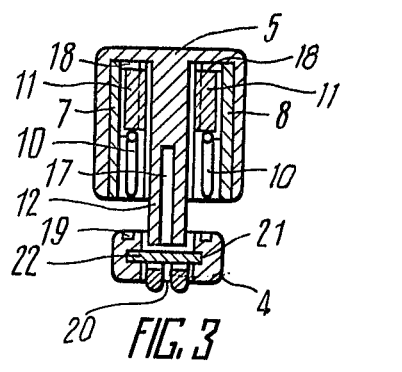
FIG. 3 is a sectional view taken on line III—III of FIG. 1.
Figure 6:
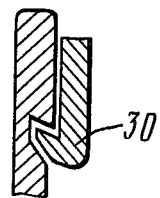
FIG. 6 is a sectional view taken on line VI—VI of FIG. 2.
Figure 4:
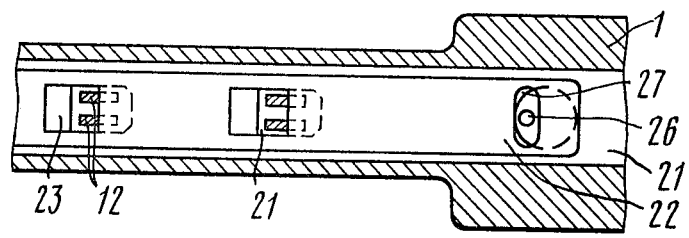
FIG. 4 is a sectional view taken on line IV—IV of FIG. 1.
Figure 5:
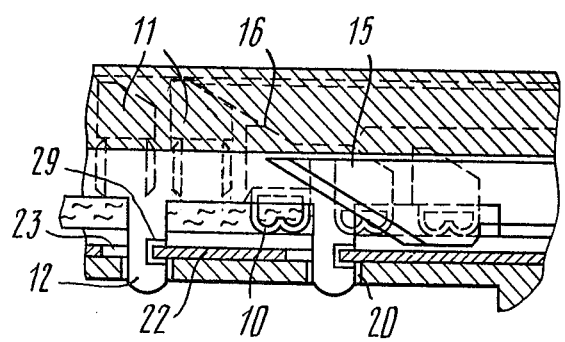
FIG. 5 illustrates on an enlarged scale the suturing of clamped tissue of an organ with staples and resection along the suture.

Referring now to the appended drawings, the surgical instrument for suturing organs includes a supporting or clinching part 1 (FIG. 1) and a staple-receiving part 2, the two parts 1 and 2 being pivotally connected with a screw 3. The working ends of the two parts 1 and 2 carry opposed longitudinal jaws 4 and 5, while their opposite ends are provided with rings 6. The longitudinal jaw 5 of the staple-receiving part 2 accommodates replaceable staple magazines 7 and 8 (FIG. 2). The staple magazines 7 and 8 have transverse slots 9 (FIG. 1) adapted to accommodate generally U-shaped staples 10 and staple drivers 11. Uniformly spaced intermediate the staple magazines 7 and 8 throughout the length of the jaw 5 are rods 12. The staple-receiving part 2 carries a slide 13, with screws 14 securing to slide 13 a knife blade 15 and two bars 16 with wedge-shaped ends, said blade and said bars being reciprocable along the three longitudinal slots 17 and 18 respectively (FIG. 3). The longitudinal jaw 4 (FIG. 1) of the supporting part 1 has made therein, in opposition to the transverse slots 9 of the staple magazines 7 and 8, indentations or anvils 19 for clinching the staples 10 (FIGS. 1 and 3). Spaced longitudinally of the jaw 4 are openings 20 (FIG. 2), their spacing corresponding to that of the rods 12 (FIG. 1), and the jaw 4 having a longitudinal slot 21 (FIG. 3) slidably accommodating a locking strip 22 (FIG. 4). The latter has apertures 23 with their spacing corresponding to that of the rods 12. The supporting part 1 (FIG. 1) carries a pin 24 retaining a screw 25 with an eccentric lug 26. This lug 26 (FIG. 4) is engageable in a slot 27 made in the locking strip 22, whereby the rotation of the screw 25 can be converted into reciprocation of the locking strip 22 (FIG. 4). The rotation of the screw 25 (FIG. 2) is limited by a pin 28. The rods 12 (FIG. 5) have grooves 29 positioned in the plane of reciprocation of the locking strip 22 (FIG. 5) when the jaws 4 (FIG. 1) and 5 are brought together to define there between a suturing gap, so that the rods 12 (FIG. 5) are engageable with the locking strip 22. With the rods 12 thus engaged by the locking strip 22, the suturing effort is transmitted by and taken up by the more rigid longitudinal jaw 5 (FIG. 1) of the staple-receiving part 2. In the position of defining the suturing gap the supporting part 1 and the staple-receiving part 2 are locked together with a latch-type lock 30 (FIG. 6).

Operation of the presently disclosed surgical instrument is illustrated by an example of performing layer-by-layer liver resection.

The longitudinal jaws 4 and 5 (FIG. 1) are spread apart. The longitudinal jaw 4 of the supporting part 1 is made to pierce the capsule of the liver. The longitudinal jaw 4 is then inserted to its full working length, with a 15 to 20 mm thick portion of the liver being between the longitudinal jaws 4 and 5. The rings 6 are brought together until the supporting part 1 and the staple-receiving part 2 are locked with the latch lock 30 (FIG. 6). When the parts 1 and 2 (FIG. 1) are thus brought together, the longitudinal jaws 4 and 5 clamp the liver portion therebetween, with all the vessel and ducts therein being accommodated in the spaces between adjacent pairs of the rods 12. The screw 25 is rotated to move the locking strip 22 (FIG. 5), with the apertures 23 being displaced accordingly and engaging the grooves 29 in the rods 12, so that a unitary rigid beam is formed with the longitudinal jaw 5 (FIG. 1) of the staple-receiving part 2. By moving the slide 13 with the knife blade 15 and the two bars 16 with the wedge-shaped ends longitudinally of the staple-receiving part 2 of the apparatus, there is performed simultaneous resection throughout the entire length of the longitudinal jaws 4 and 5, and suturing with the staples 10 of the removed portion of the liver and of the remaining one. The slide 13 is then returned into its initial position. The screw 25 is rotated into its initial position to release the rods 12 from the engagement with the locking strip 22. The longitudinal jaws are spread apart, and the instrument is taken off the sutured portion of the liver. The staple magazines 7 and 8 (FIG. 2) are replaced, and the abovedescribed operating cycle is repeated to perform resection and suturing of the entire thickness of the liver portion. The liver portions 15 to 20 mm thick are thus resected and sutured in a single cycle, while liver portions of the maximum thickness in a human being require 3 to 4 such cycles.

The instrument is operable for resection surgery of the affected portions of the spleen, lungs and other organs, and also as an organ suturing instrument.

What we claim is:

1. A surgical instrument for suturing organs, such as parenchymal organs, comprising:
   a supporting part having a working end;
   a staple-receiving part having a working end, said staple-receiving part being pivotally connected with said supporting part;
   a first longitudinal jaw of generally rectangular cross-section carried by the working end of said supporting part;
   a second longitudinal jaw carried by the working end of said staple-receiving part in opposition to said first longitudinal jaw;
   staples having two legs, the whole being generally "U" shaped;
   indentations in said first longitudinal jaw for bending over the legs of staples;
   longitudinal staple magazines accommodated in said second longitudinal jaw, each of said magazines confining and spacing a plurality of single staples along said second longitudinal jaw;
   sliding members for driving said staples,
   transverse guide slots formed in said staple magazines in opposition to said indentations, to accommodate therein staples and said sliding members for driving said staples;
   longitudinal slots in said staple magazines;
   bars with wedge-shaped ends facing said members for driving said staples, and accommodated in said longitudinal slots for direct communication and cooperation with said staple-driving members, for driving out and bending over the legs of said staples;
   a separate longitudinal slot located between said longitudinal slots in said staple-receiving part;
   a knife blade movably accommodated in said longitudinal slot in said staple-receiving part for motion jointly with said bars;
   a latch-type locking means for preventing substantial traumatisim of layer-by-layer sutured organs and for ensuring rigid aligment of said jaws of the instrument in the course of a suturing operation; said means comprising:
   rods attached to said second longitudinal jaw in two parallel longitudinal rows and projecting from the medial surface thereof;
   transverse grooves in said rods near their medial ends;
   a longitudinal guide slot in said first longitudinal jaw;
   jaw openings spaced in said first longitudinal jaw for receiving a portion of said rods;
   a locking strip slidably engaged in said longitudinal guide slot, said strip having apertures therein which are alignable with said jaw openings;
   manual means for sliding said locking strip within said longitudinal guide slot so that when said rods have been received in said openings the rim of said apertures is slidably engagable in said transverse grooves, thus locking the jaws together.

* * * * *